(12) United States Patent
Oshima

(10) Patent No.: US 9,339,214 B2
(45) Date of Patent: May 17, 2016

(54) BODY MOVEMENT DETECTION DEVICE

(75) Inventor: Yoshitake Oshima, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 690 days.

(21) Appl. No.: 13/527,152

(22) Filed: Jun. 19, 2012

(65) Prior Publication Data

US 2012/0265480 A1 Oct. 18, 2012

Related U.S. Application Data

(63) Continuation of application No. PCT/JP2011/050638, filed on Jan. 17, 2011.

(30) Foreign Application Priority Data

Jan. 20, 2010 (JP) .................................. 2010-010107

(51) Int. Cl.
*A61B 5/11* (2006.01)
*A61B 5/00* (2006.01)

(52) U.S. Cl.
CPC ............ *A61B 5/1116* (2013.01); *A61B 5/1123* (2013.01); *A61B 5/1118* (2013.01); *A61B 5/6823* (2013.01); *A61B 2560/0242* (2013.01); *A61B 2560/0257* (2013.01); *A61B 2562/0219* (2013.01)

(58) Field of Classification Search
CPC ............... A61B 5/1118; A61B 5/1123; G06F 9/300032; G06F 9/30032
USPC ........................................................ 702/150
See application file for complete search history.

(56) References Cited

U.S. PATENT DOCUMENTS

2007/0072158 A1 3/2007 Unuma et al.
2008/0077326 A1* 3/2008 Funk et al. .................... 701/220
2009/0018797 A1* 1/2009 Kasama et al. ............... 702/160

(Continued)

FOREIGN PATENT DOCUMENTS

JP     A-11-347021     12/1999
JP     A-2002-034937     2/2002

(Continued)

OTHER PUBLICATIONS

Eves, "A Workplace Intervention to Promote Stair Climbing: Greater Effects in the Overweight", Obesity vol. 14 No. 12 Dec. 2006.*

(Continued)

*Primary Examiner* — Gregory J Toatley
*Assistant Examiner* — Michael Dalbo
(74) *Attorney, Agent, or Firm* — Oliff PLC

(57) ABSTRACT

A body movement detection device is provided with a main body, a display unit, and a control unit, the control unit including an ascent/descent method detection unit that detects whether a user who is wearing or carrying the main body is ascending/descending using a lift device, a counting unit that counts the number of times that the user ascends/descends using the lift device and the number of times that the user ascends/descends without using the lift device, based on the detection result of the ascent/descent method detection unit, and a display control unit that causes the display unit to display each of the values counted by the counting unit. The method by which the user ascends/descends can thereby be clearly displayed.

4 Claims, 14 Drawing Sheets

(56) References Cited

U.S. PATENT DOCUMENTS

2010/0318293 A1* 12/2010 Brush et al. .................. 701/211
2011/0131005 A1   6/2011 Ueshima et al.

FOREIGN PATENT DOCUMENTS

| JP | A-2005-230340 | 9/2005 |
| JP | A-2007-093433 | 4/2007 |
| JP | A-2008-220517 | 9/2008 |
| JP | A-2008-262522 | 10/2008 |
| JP | A-2009-018103 | 1/2009 |
| WO | WO 2009/078114 A1 | 6/2009 |

OTHER PUBLICATIONS

Jan. 13, 2014 Office Action issued in Chinese Patent Application No. 201180006659.2 (with English translation).
Sep. 17, 2013 Office Action issued in Japanese Patent Application No. 2010-010107 (with translation).
International Search Report issued in Application No. PCT/JP2011/050638; Dated Feb. 15, 2011 (With Translation).

* cited by examiner

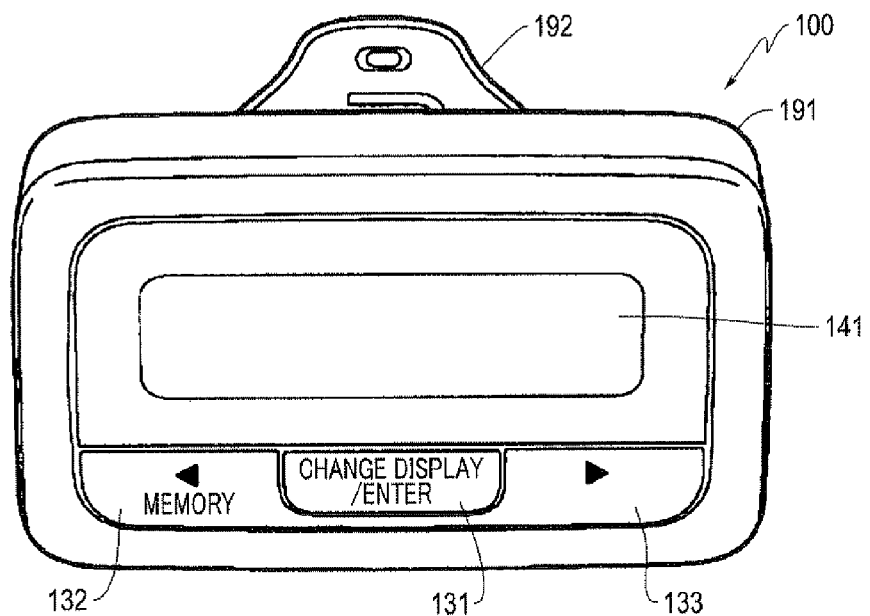
FIG. 1
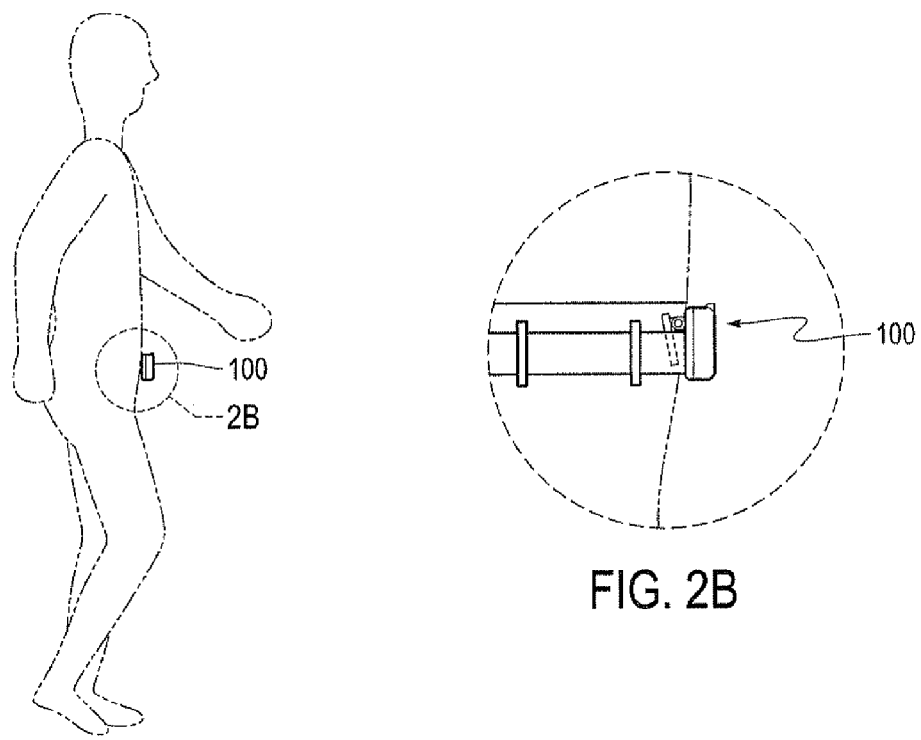
FIG. 2A
FIG. 2B

BODY MOVEMENT DETECTION DEVICE

This is a Continuation of International Application No. PCT/JP2011/050638 filed Jan. 17, 2011, which claims the benefit of Japanese Application No. 2010-010107 filed Jan. 20, 2010. The disclosure of the prior applications are hereby incorporated by reference herein in their entirety.

TECHNICAL FIELD

This invention relates to a body movement detection device, and more particularly to a body movement detection device suitable for detecting body movement relating to walking or running.

BACKGROUND ART

Conventionally, there are calories burned calculation devices having an acceleration sensor that outputs detection values for performing state determination as to whether a person being measured is walking or running depending on the impact between the person's heel and the ground, and an atmospheric pressure sensor for detecting change in atmospheric pressure according to ascending/descending movement and determining the ascending/descending action of the person, and being capable of calculating calories burned according to the state of physical activity, based on the acceleration signals from the acceleration sensor that depend on the action of the person and detection signals from the atmospheric pressure sensor that depend on the change in atmospheric pressure (see Patent Literature 1).

CITATION LIST

Patent Literature

Patent Literature 1: JP 11-347021A

SUMMARY OF INVENTION

Technical Problem

However, there is a problem in that, according to the calories burned calculation device of Patent Literature 1, the method by which the person being measured ascends/descends is unclear.

The invention was made in order to solve an abovementioned problem, and has as one object to provide a body movement detection device capable of clearly displaying the method by which the person being measured ascends/descends.

Solution of Problem

In order to attain the abovementioned object, according to an aspect of the invention, a body movement detection device includes a main body, a display unit and a control unit, the control unit including an ascent/descent method detection unit that detects whether a user who is wearing or carrying the main body is ascending/descending using a lift device, a counting unit that counts the number of times that the user ascends/descends using the lift device and the number of times that the user ascends/descends without using the lift device, based on a detection result of the ascent/descent method detection unit, and a display control unit that causes the display unit to display each of the values counted by the counting unit.

According to this invention, the body movement detection device detects whether a user who is wearing or carrying the main body ascends/descends using a lift device, counts the number of times that the user ascends/descends using a lift device and the number of times that the user ascends/descends without using a lift device, based on the detection results, and displays the respective counted values on a display unit.

The number of times that the user ascends/descends using a lift device and the number of times that the user ascends/descends without using a lift device are thus displayed. As a result, a body movement detection device capable of clearly displaying the method by which the user ascends/descends can be provided.

Preferably, the counting unit counts the number of times that the user ascends/descends using the lift device and the number of times that the user ascends/descends without using the lift device, per ascent and descent.

According to this invention, the body movement detection device counts and displays the number of times that the user ascends using a lift device, the number of times that the user descends using a lift device, the number of times that the user ascends without using a lift device, and the number of times that the user descends without using a lift device. The method by which the user ascends/descends can thus be clearly displayed respectively for ascending or descending.

Preferably, the counting unit counts the number of times that the user ascends/descends using the lift device and the number of times that the user ascends/descends without using the lift device, per number of ascended/descended floors.

According to this invention, the body movement detection device displays the number of times that the user ascends/descends using a lift device and the number of times that the user ascends/descends without using a lift device per number of ascended/descended floors. The method by which the user ascends/descends can thus be clearly displayed in terms of the number of ascended/descended floors.

Preferably, the body movement detection device further includes an acceleration sensor that detects acceleration of the main body, and an atmospheric pressure sensor that detects an ambient atmospheric pressure of the main body, and the ascent/descent method detection unit detects whether the user is ascending/descending using the lift device, based on a detection result from the acceleration sensor and a detection result from the atmospheric pressure sensor.

According to this invention, the body movement detection device detects whether the user ascends/descends using a lift device, based on detection results from an acceleration sensor and an atmospheric pressure sensor. It can thus be detected whether the user ascends/descends using a lift device, without using sensors other than an acceleration sensor and an atmospheric pressure sensor.

BRIEF DESCRIPTION OF DRAWINGS

FIG. 1 is an external view of an activity monitor according to embodiments of the invention.

FIGS. 2A and 2B are diagrams showing the activity monitor in use according to the embodiments.

DESCRIPTION OF EMBODIMENTS

Figure 3:
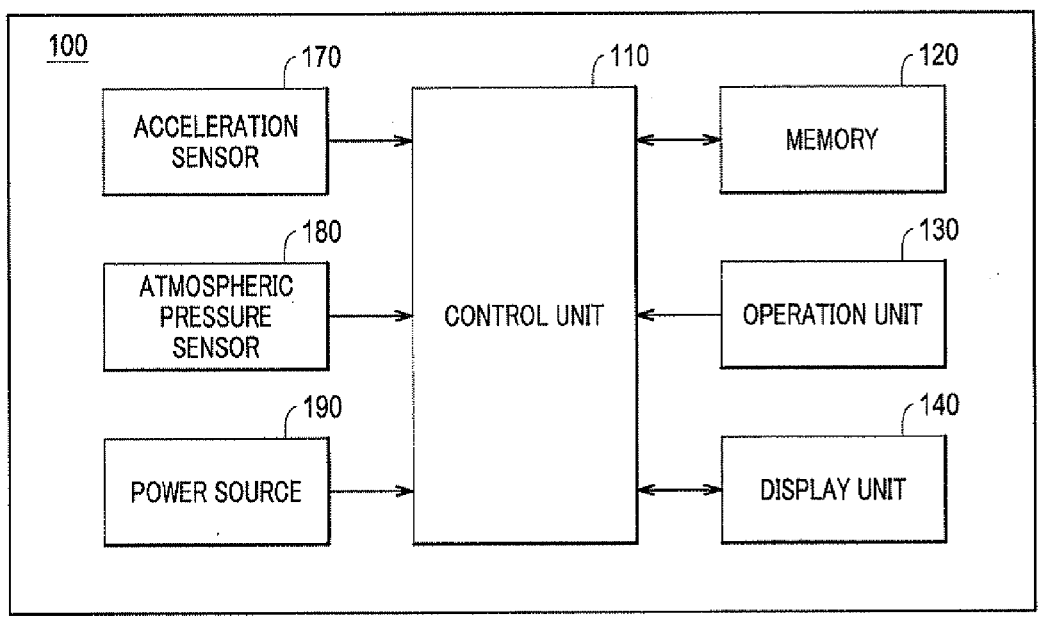
FIG. 3 is a block diagram showing a schematic configuration of the activity monitor according to the embodiments.

Hereinafter, embodiments of the invention will be described in detail with reference to the drawings. Note that the same reference numerals are given to the same or corresponding parts in the drawings, and description thereof will not be repeated.

The embodiments are described in terms of the body movement detection device being an activity monitor capable of measuring not only the number of steps but also the amount of activity that a user undertakes in physical activity, daily life and the like (e.g., vacuuming, light load carrying, cooking, etc.). However, the present invention is not limited thereto, and the body movement detection device may be a pedometer capable of measuring the number of steps.

First Embodiment

FIG. 1 is an external view of an activity monitor 100 according to embodiments of the invention. Referring to FIG. 1, the activity monitor 100 is primarily constituted by a main body 191 and a clip 192. The clip 192 is used in order to attach the activity monitor 100 firmly to the user's clothing or the like.

The main body 191 is provided with a change display/enter switch 131, a left operation/memory switch 132 and a right operation switch 133 constituting part of an operation unit 130 that is discussed later, and a display 141 constituting part of a display unit 140 that is discussed later.

The display 141 is constituted by a liquid crystal display (LCD) in the present embodiment, but is not limited thereto and may be another type of display such as an electroluminescence (EL) display.

FIG. 2A is a diagram showing the activity monitor 100 in use according to the embodiments. Referring to FIG. 2B, the activity monitor 100 is, for example, attached to a belt around the user's waist using the clip 192.

Note that the present invention is not limited thereto, and the activity monitor 100 may be designed so as to be used while being attached to another part of the user's body, or may be designed so as to be used while being carried by the user in a bag or the like.

FIG. 3 is a block diagram showing a schematic configuration of the activity monitor in the embodiments. Referring to FIG. 3, the activity monitor 100 includes a control unit 110, a memory 120, the operation unit 130, the display unit 140, an acceleration sensor 170, an atmospheric pressure sensor 180, and a power source 190. Also, the activity monitor 100 may be configured to include a warning sound unit for outputting sounds, an interface for communicating with an external computer, and the like.

The control unit 110, the memory 120, the operation unit 130, the display unit 140, the acceleration sensor 170, the atmospheric pressure sensor 180, and the power source 190 are built into the main body 191 illustrated in FIG. 1.

The operation unit 130 includes the change display/enter switch 131, the left operation/memory switch 132 and the right operation switch 133 illustrated in FIG. 1, and transmits operation signals indicating that these switches have been operated to the control unit 110.

The acceleration sensor 170 used may be a semiconductor sensor based on micro-electro-mechanical systems (MEMS) technology, but is not limited thereto, and may be another type of sensor such as a mechanical sensor or an optical sensor. The acceleration sensor 170, in the embodiments, outputs detection signals indicating acceleration in three axis directions to the control unit 110. However, the acceleration sensor 170 is not limited to a triaxial sensor, and may be a single-axis sensor or a biaxial sensor.

The atmospheric pressure sensor 180 used is based on MEMS technology, but is not be limited thereto, and may be another type of sensor. The atmospheric pressure sensor 180 outputs detection signals indicating ambient atmospheric pressure values to the control unit 110.

The memory 120 includes a nonvolatile memory such as read-only memory (ROM; e.g., flash memory), and a volatile memory such as random access memory (RAM; e.g., synchronous dynamic random access memory (SDRAM)).

The memory 120 stores the data of programs for controlling the activity monitor 100, data used in order to control the activity monitor 100, setting data for setting the various functions of the activity monitor 100, and measurement result data per prescribed time period (e.g., daily) such as number of steps and amount of activity. The memory 120 is also used as a work memory when programs are executed.

The control unit 110 includes a central processing unit (CPU), and, in accordance with the programs for controlling the activity monitor 100 stored in the memory 120, controls the memory 120 and the display unit 140 according to operation signals from the operation unit 130, based on detection signals from the acceleration sensor 170 and the atmospheric pressure sensor 180.

The display unit 140 includes the display 141 illustrated in FIG. 1, and controls the display 141 to display prescribed information adhering to control signals from the control unit 110.

The power source 190 includes a replaceable battery, and supplies power from the battery to components requiring power so as to operate the control unit 110 and the like of the activity monitor 100.

Figure 4A:
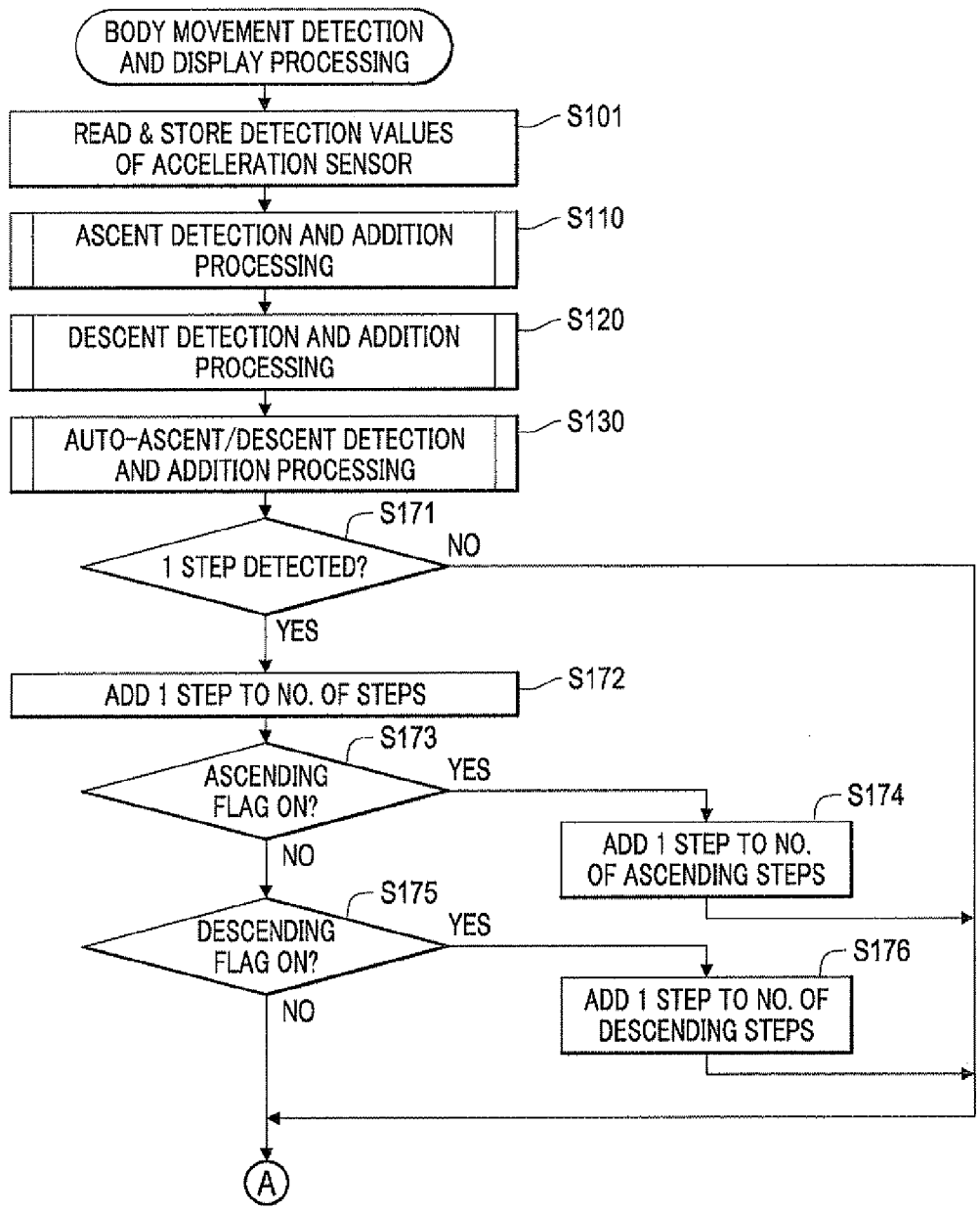
FIGS. 4A and 4B are flowcharts showing the flow of body movement detection and display processing executed by the activity monitor according to a first embodiment.

FIG. 4A is a flowchart showing the flow of the body movement detection and display processing executed by the activity monitor 100 according to a first embodiment. Referring to FIG. 4A, at step S101, the control unit 110 reads the detection values for acceleration along three axes indicated by the detection signals from the acceleration sensor 170, and stores the read detection values in the memory 120. The memory 120 sequentially stores detection values for acceleration along three axes at prescribed intervals of a prescribed length (e.g., several milliseconds, tens of milliseconds) each time step S101 is executed.

Figure 5:
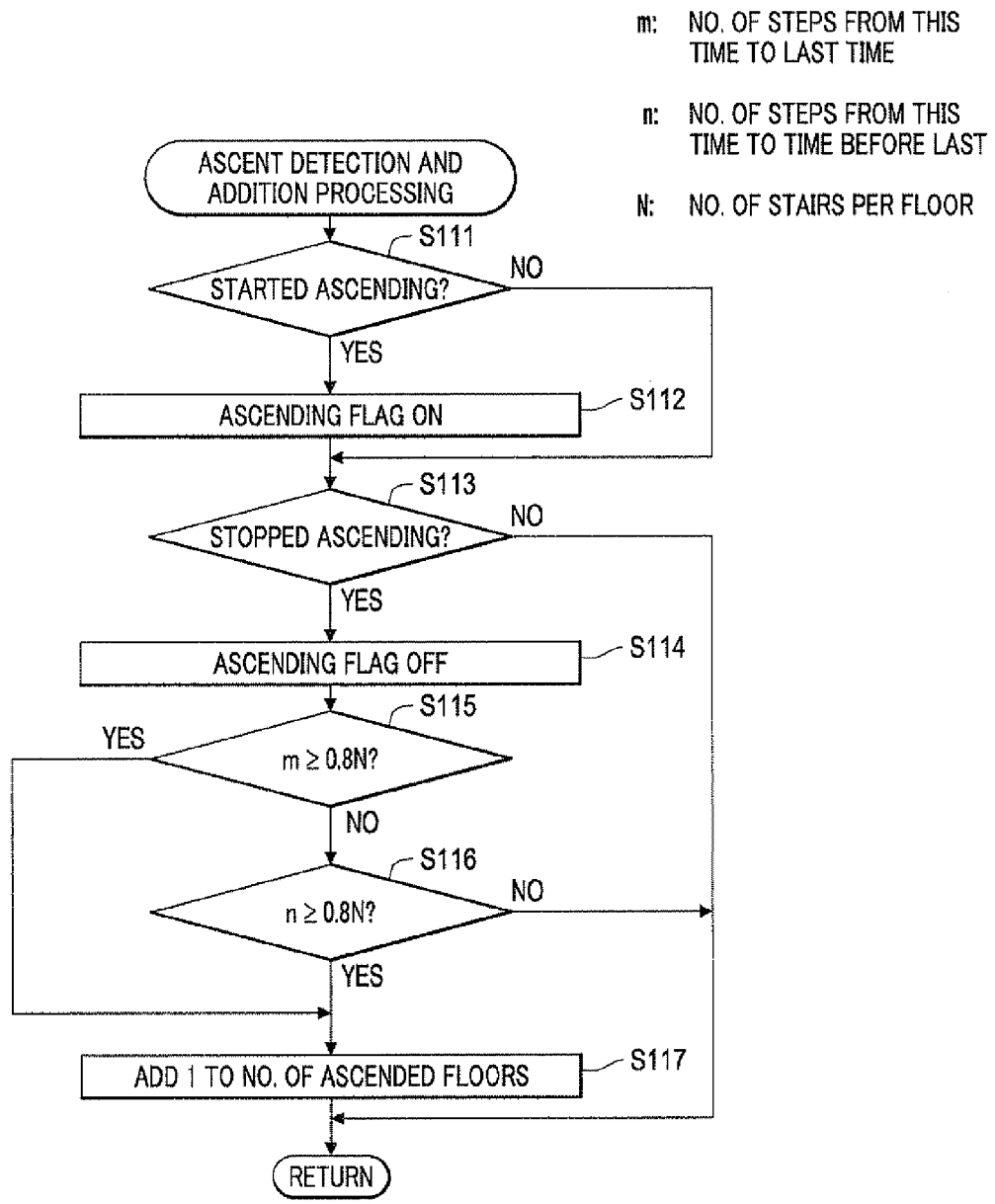
FIG. 5 is a flowchart showing the flow of ascent detection and addition processing executed by the activity monitor according to the first embodiment.

Next, at step S110, the control unit 110 executes ascent detection and addition processing. FIG. 5 is a flowchart showing the flow of the ascent detection and addition processing executed by the activity monitor according to the first embodiment.

Referring to FIG. 5, at step S111, the control unit 110 judges whether the user who is wearing or carrying the activity monitor has started ascending stairs, an incline or the like by walking.

Figure 7:
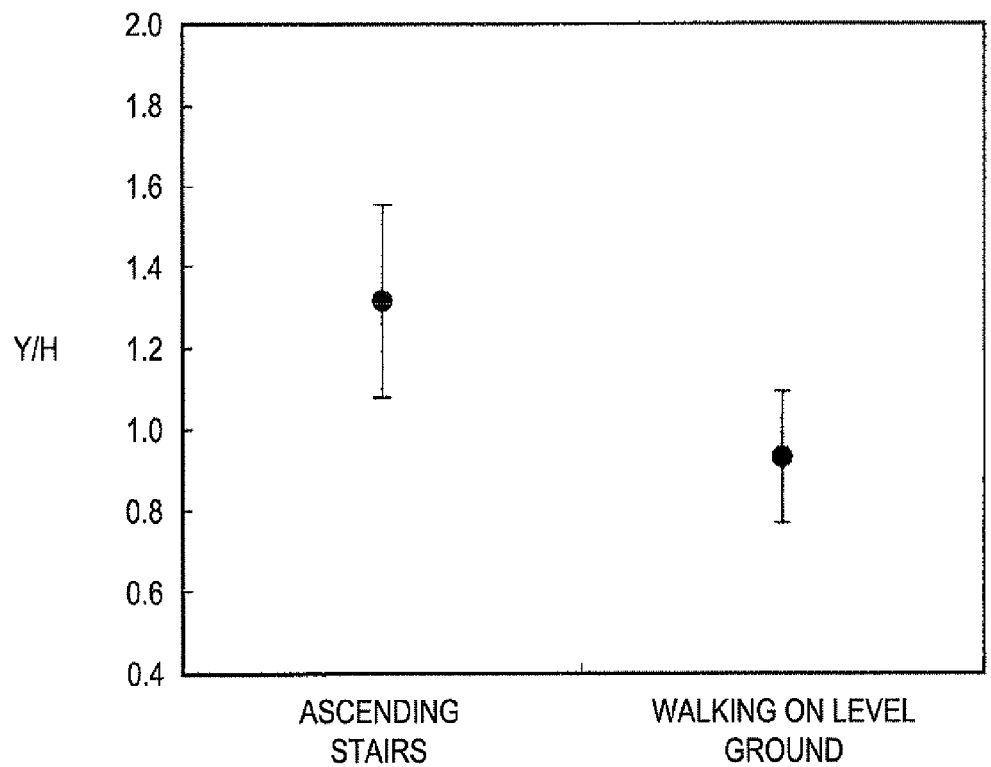
FIG. 7 is a graph showing differences in an index relating to acceleration due to differences in the form of physical activity.

FIG. 7 is a graph showing differences in an index relating to acceleration due to differences in the form of physical activity. Referring to FIG. 7, the judgment at step S111 of FIG. 5 as to whether the user has started ascending is performed as follows.

First, accumulated sums of acceleration X, Y and Z are calculated using equations (1) to (3), with regard to N detection values xi, yi, and zi (i=1 to N) for the most recent short interval that are indicated by the three detection signals for acceleration in the left-right (x-axis), up-down (y-axis) and front-back (z-axis) directions obtained from the triaxial acceleration sensor 170, these values having been stored in the memory 120 at the aforementioned step S101 in FIG. 4.

Equation 1
$$X = \frac{\sum_{i}^{N} |x_i|}{N} \quad (1)$$

Equation 2
$$Y = \frac{\sum_{i}^{N} |y_i|}{N} \quad (2)$$

Equation 3
$$Z = \frac{\sum_{i}^{N} |z_i|}{N} \quad (3)$$

Next, the accumulated sum of horizontal acceleration H obtained by combining the left-right and front-back accelerations is calculated using equation (4).

Equation 4
$$H = \sqrt{X^2 + Z^2} \quad (4)$$

A ratio Y/H of the accumulated sum of up/down acceleration Y and the accumulated sum of horizontal acceleration H is then calculated.

As shown by the graph of FIG. 7, test results indicate that in the case where the user is walking on level ground, the ratio of horizontal acceleration to up-down acceleration is roughly 1:1, and the Y/H value is in the vicinity of 0.9. Also, in the case where the user is ascending stairs, up-down acceleration increases over horizontal acceleration, and Y/H value is in the vicinity of 1.3.

By setting the threshold at 1.1, which is the midpoint of Y/H values in both cases, based on the test results, it is judged that the user is ascending stairs if Y/H≥1.1, and that the user is walking on level ground if Y/H<1.1.

Here, although the cases where the user ascends stairs and walks on level ground are described, it can be judged whether the user is descending stairs based on similar test results. Also, although the case where the user is walking is described, it can be judged whether the user is running based on similar test results.

Note that in the present embodiment, it is judged whether the user has started ascending, using detection values from an acceleration sensor. However, the present invention is not limited thereto, and it may be judged whether the user has started ascending, using detection values from an atmospheric pressure sensor. Specifically, when the user starts ascending, the atmospheric pressure indicated by the detection values of the atmospheric pressure sensor will fall. It is thus judged whether the user has started ascending by judging whether the atmospheric pressure has fallen.

Returning to FIG. 5, if it is judged at step S111 that the user has started ascending by walking (if judged YES), the control unit 110, at step S112, sets an ascending flag indicating that the user is currently ascending to ON. The ascending flag is stored in the memory 120.

If it is judged at step S111 that the user has not started ascending by walking (if judged NO), or after step S112, the control unit 110, at step S113, judges whether the user has stopped ascending by walking. The judgment as to whether the user has stopped ascending by walking can be performed similarly to the abovementioned judgment as to whether the user has started ascending by walking.

If it is judged that the user has stopped ascending by walking (if judged YES at step S113), the control unit 110, at step S114, sets the ascending flag stored in the memory 120 to OFF.

Next, at step S115, the control unit 110 judges whether a number of steps m obtained by subtracting the accumulated number of steps when it was judged that the user started ascending last time from the accumulated number of steps when it was judged that the user stopped ascending this time, or in other words, the number of steps m after the user started ascending last time until the user stopped ascending this time, is greater than or equal to 0.8 times the number of stairs N equivalent to one floor (e.g., 13 stairs).

If it is judged that the number of steps m is not greater than or equal to 0.8 times N (if judged NO at step S115), the control unit 110, at step S116, judges whether a number of steps n obtained by subtracting the accumulated number of steps when it was judged that the user started ascending the time before last from the accumulated number of steps when it was judged that the user stopped ascending this time, or in other words, the number of steps n after the user started ascending the time before last until the user stopped ascending this time, is greater than or equal to 0.8 times the number of stairs N for one floor.

If it is judged that the number of steps m from last time until this time is greater than or equal to 0.8 times N (if judged YES at step S115), or if it is judged that the number of steps n from the time before last until this time is greater than or equal to 0.8 times N (if judged YES at step S116), the control unit 110, at step S117, adds 1 to number of floors that the user has ascended. The number of ascended floors is stored in the memory 120.

If it is judged that the user has not stopped ascending by walking (if judged NO at step S113), if it is judged that the number of steps n from the time before last until this time is less than 0.8 times N (if judged NO at step S116), or after step S117, the control unit 110 returns to the body movement detection and display processing from which the ascent detection and addition processing was originally called.

In the case of stairs, it will be judged not only at the landing on each floor but also at a landing between floors (e.g., in the middle of floors) that the user started ascending at step S111 and that the user stopped ascending at step S113. In view of this, when it is judged, in the processing of steps S113 to S117, that the user has stopped ascending, 1 is added to the number of ascended floors when it is judged that the number of steps from last time until this time has reached roughly the number of stairs for one floor, having judged that the user has ascended roughly one flight of stairs that do not have a landing between floors, whereas 1 is added to the number of ascended floors when it is judged that the number of steps from the time before last until this time has reached roughly the number of stairs for one floor, having judged that the user has ascended roughly one flight of stairs that do have a landing between floors.

Although it is thus judged whether the differences in number of steps m and n are greater than or equal to 0.8 times the number of stairs N for one floor, the scaling factor is not limited to 0.8 times, and any scaling factor that enables it to be judged that the number of steps has reached roughly the number of stairs for one floor may be used.

Also, although the number of stairs N for one floor was given as 13, for example, the number of stairs N for one floor may be another value, because there are often around 13 stairs in the case of residential houses, and 13 stairs or more in the case of office buildings and apartments. Also, a configuration may be adopted in which the user is able to set the number of stairs N for one floor himself or herself, according to the stair count of the stairs that he or she normally uses.

Note that the time at which the user started ascending last time denotes the time at which the user started ascending one flight of stairs that do not have a landing. Thus, a configuration may be adopted such that in the case where the number of steps obtained by subtracting the accumulated number of steps when the user started ascending last time from the accumulated number of steps when it was judged that the user stopped ascending this time is extremely large (e.g., greater than or equal to twice the number of stairs N for one floor), 1 is not added to the number of ascended floors in this case, because it is possible that the stairs from which the user is judged to have started ascending last time differ from the stairs on which the user is judged to have stopped ascending this time.

Similarly, the time at which the user started ascending the time before last denotes the time at which the user started ascending one flight of stairs that have a landing. Thus, a configuration may be adopted such that in the case where the number of steps obtained by subtracting the accumulated number of steps when the user started ascending the time before last from the accumulated number of steps when it was judged that the user stopped ascending this time is extremely large (e.g., greater than or equal to twice the number of stairs N for one floor), 1 is not added to the number of ascended floors in this case, because it is possible that the stairs from which the user is judged to have started ascending the time before last differ from the stairs on which the user is judged to have stopped ascending this time.

Returning to FIG. 4A, after execution of the ascent detection and addition processing of step S110, the control unit 110, at step S120, executes descent detection and addition processing. This descent detection and addition processing is realized by exchanging "ascent" for "descent" in the ascent detection and addition processing illustrated in FIG. 5.

Figure 6:
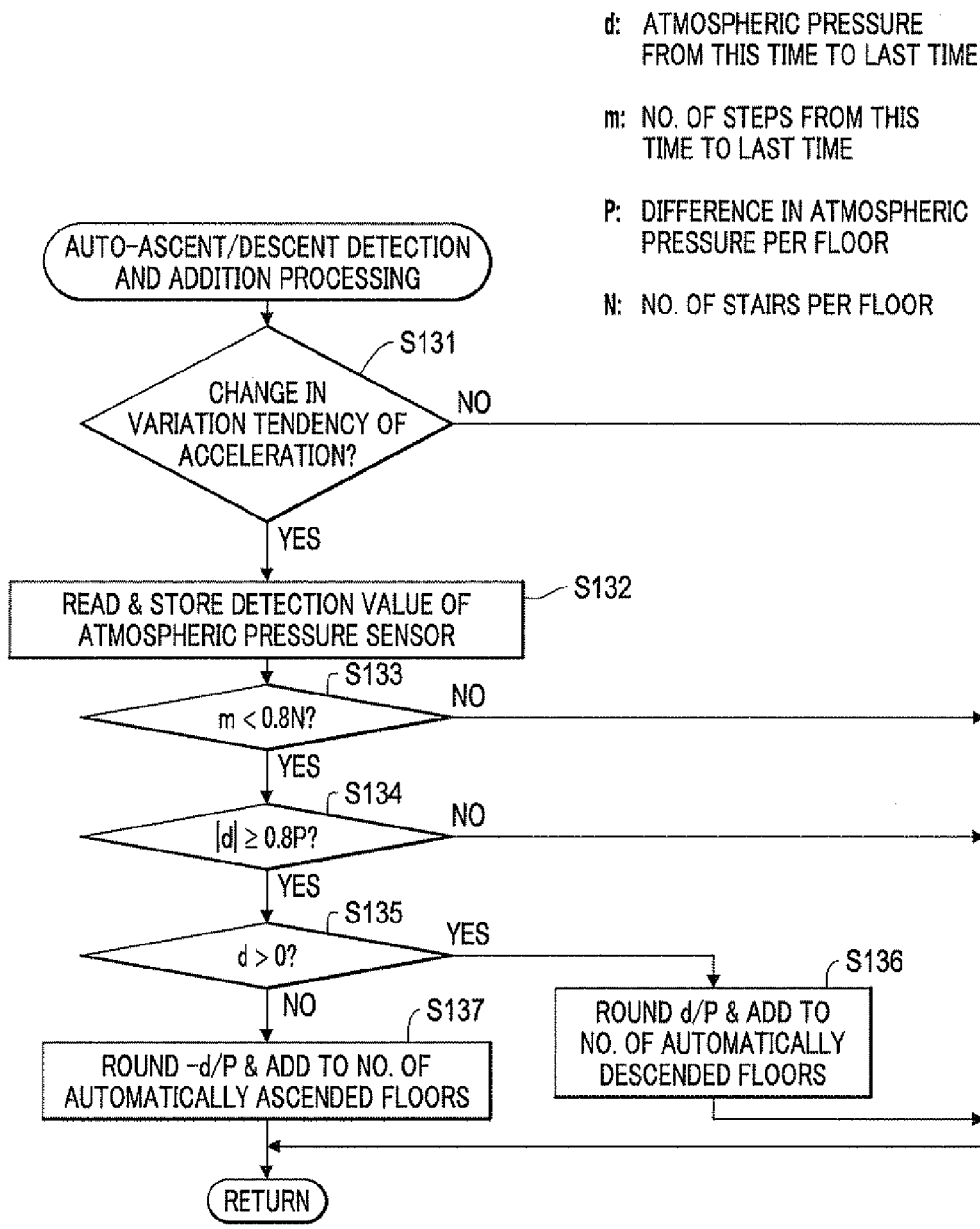
FIG. 6 is a flowchart showing the flow of auto-ascent/descent detection and addition processing executed by the activity monitor according to the first embodiment.

Next, at step S130, the control unit 110 executes auto-ascent/descent detection and addition processing. FIG. 6 is a flowchart showing the flow of the auto-ascent/descent detection and addition processing executed by the activity monitor 100 according to the first embodiment.

Referring to FIG. 6, at step S131, the control unit 110 judges whether there has been a change in the variation tendency of detection values indicated by detection signals from the acceleration sensor 170. Specifically, in the case where the user starts or stops ascending or descending stairs, an incline, or the like such as described at the aforementioned step S111 in FIG. 5, or in the case where the user starts or stops ascending or descending using a lift device such as an elevator or an escalator, there will be some sort of change in the variation tendency of detection values from the acceleration sensor 170.

If it is judged that there has been a change in the variation tendency of detection values for acceleration (if judged YES at step S131), the control unit 110, at step S132, reads the detection value indicated by the detection signal from the atmospheric pressure sensor 180, and stores the read detection value in the memory 120.

Next, at step S133, the control unit 110 judges whether the number of steps m obtained by subtracting the accumulated number of steps when it was judged that there was a change in the variation tendency of acceleration last time from the accumulated number of steps when it was judged that there was a change in the variation tendency of acceleration this time, or in other words, the number of steps in after there was a change in the variation tendency of acceleration last time until there was a change in the variation tendency of acceleration this time, is less than 0.8 times of the number of stairs N equivalent to one floor (e.g., 13 stairs).

If it is judged that the number of steps m from last time until this time is less than 0.8 times the number of stairs N for one floor (if judged YES at step S133), the control unit 110, at step S134, judges whether a difference in atmospheric pressure d obtained by subtracting the detection value for atmospheric pressure when it was judged that there was a change in the variation tendency of acceleration last time from the detection value for atmospheric pressure when it was judged that there was a change in the variation tendency of acceleration this time, or in other words, the absolute value of the difference in atmospheric pressure d after there was a change in the variation tendency of acceleration last time until there was a change in the variation tendency of acceleration this time, is greater than or equal to 0.8 times a difference in atmospheric pressure P equivalent to one floor (e.g., 0.3 hPa).

If it is judged that the absolute value $|d|$ of the difference in atmospheric pressure between last time and this time is greater than or equal to 0.8 times the difference in atmospheric pressure P for one floor (if judged YES at step S134), the control unit 110, at step S135, judges whether the difference in atmospheric pressure d between last time and this time is greater than zero, or in other words, whether the difference in atmospheric pressure d is positive.

If it is judged that the difference in atmospheric pressure d is positive (if judged YES at step S135), the control unit 110, at step S136, adds a value obtained by dividing the difference in atmospheric pressure d between last time and this time by the difference in atmospheric pressure P for one floor and rounding the resultant value to the number of automatically descended floors, which is the accumulated value of the number of floors that the user has descended using a lift device. The number of automatically descended floors is stored in the memory 120.

On the other hand, if it is judged that the difference in atmospheric pressure d is not positive (if judged NO at step S135), the control unit 110, at step S137, adds a value obtained by dividing the difference in atmospheric pressure d between last time and this time by the difference in atmospheric pressure P for one floor, reversing the plus/minus sign and rounding the resultant value to the number of automatically ascended floors, which is the accumulated value of the number of floors that the user has ascended using a lift device. The number of automatically ascended floors is stored in the memory 120.

If it is judged that there is no change in the variation tendency of acceleration (if judged NO at step S131), if it is judged that the number of steps m from last time until this time is not less than 0.8 times the number of stairs N for one floor (if judged NO at step S133), if it is judged that the absolute value |d| of the difference in atmospheric pressure between last time and this time is not greater than or equal to 0.8 times the difference in atmospheric pressure P for one floor (if judged NO at step S134), or after step S136 or step S137, the control unit 110 returns to the body movement detection and display processing from which this auto-ascent/descent detection and addition processing was originally called.

In this way, it is clear when the user is deemed to have ridden the lift device and when the user is deemed to have alighted the lift device as a result of changes in the variation tendency of acceleration, and when it is judged that the difference in atmospheric pressure between when the user is deemed to have ridden the lift device and when the user is deemed to have alighted the lift device has reached roughly the difference in atmospheric pressure P for one floor, it is judged that the user has ascended/descended using a lift device, and the number of floors that the user has ascended/descended this time, which is calculated by dividing the difference in atmospheric pressure d by the difference in atmospheric pressure P for one floor, is added to the number of automatically descended floors in the case where the user has descended and to the number of floors automatically ascended in the case where the user has ascended, despite it being deemed that the difference in number of steps between the accumulated number of steps when the user is deemed to have ridden the lift device and the accumulated number of steps when the user is deemed to have alighted the lift device has not reached the number of stairs N for one floor.

Thus, while it is judged whether the difference in atmospheric pressure d and the number of steps m are respectively greater than or equal to 0.8 times the difference in atmospheric pressure P for one floor and the number of stairs N for one floor, the scaling factor is not limited to 0.8, and any scaling factor that enables it to be judged that the respective differences have reached roughly the number of stairs for one floor may be used.

Also, the difference in atmospheric pressure P for one floor was given as 0.3 hPa, assuming a floor height of 3 m for one floor of a residential house. However, the present invention is not limited thereto, and differences in atmospheric pressure P for one floor of 0.5 hPa and 0.4 hPa, respectively assuming a floor height of 5 m for one floor of an office building and 4 m for one floor of an apartment, may be used. The difference in atmospheric pressure P for one floor may also take other values. Also, a configuration may be adopted in which the user is able to set the difference in atmospheric pressure P for one floor himself or herself, according to the floor height of the building that he or she normally uses. Note that it is assumed that atmospheric pressure falls by 0.1 hPa for every meter in floor height gained.

Returning to FIG. 4A, after step S130, the control unit 110, at step S171, judges whether one step of walking or running has been detected, based on the detection values from the acceleration sensor 170. A conventional technique can be used for detecting the number of steps from the detection values for acceleration.

If it is judged that one step was detected (if judged YES at step S171), the control unit 110, at step S172, adds one step to the accumulated number of steps. The accumulated number of steps is stored in the memory 120.

Furthermore, at step S173, the control unit 110 judges whether the ascending flag was set to ON at the aforementioned step S112 in FIG. 5. If it is judged that the ascending flag is ON (if judged YES at step S173), the control unit 110, at step S174, adds one step to the number of ascending steps, which is the accumulated number of steps when the user has ascended stairs, an incline or the like. The number of ascending steps is stored in the memory 120.

On the other hand, if it is judged that the ascending flag is not ON (if judged NO at step S173), the control unit 110, at step S175, judges whether a descending flag has been set to ON in the descent detection and addition processing of step S120. If it is judged that the descending flag is ON (if judged YES at step S175), the control unit 110, at step S176, adds one step to the number of descending steps, which is the accumulated number of steps when the user has descended stairs, an incline or the like. The number of descending steps is stored in the memory 120.

In this way, the number of steps according to the form of physical activity, such as whether the user is walking on level ground or ascending or descending, can be counted. Note that although the form of physical activity is given here as walking on level ground, ascending by walking or descending by walking, the present invention is not limited thereto, and other forms of activity may be included, such as a running on level ground, ascending by running or descending by running.

If it is judged that one step has not been detected (if judged NO at step S171), or after step S174 or step S176, the control unit 110, at step S181, judges whether the number of ascended floors described at step S117 of FIG. 5 and the number of automatically ascended floors described at step S137 of FIG. 6 are being displayed, or whether an operation for switching display to the number of ascended floors and the number of automatically ascended floors has been performed as a result of the change display/enter switch 131 of the operation unit 130 being operated.

If it is judged that the number of ascended floors and the number of automatically ascended floors are being displayed, or that display has been switched to the number of ascended floors and the number of automatically ascended floors (if judged YES at step S181), the control unit 110, at step S182, respectively reads out, from the memory 120, the number of ascended floors counted and stored in the memory 120 at step S117 of FIG. 5, and the number of automatically ascended floors counted and stored in the memory 120 at step S137 of FIG. 6, and transmits a control signal to the display unit 140 so as to cause the read values to be displayed on the display 141.

Figure 8:
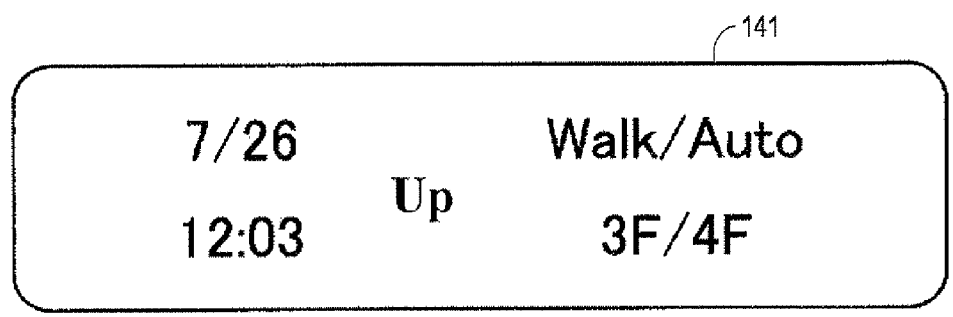
FIG. 8 shows a first exemplary display that is displayed on the activity monitor according to the first embodiment.

FIG. 8 shows a first exemplary display that is displayed on the activity monitor 100 according to the first embodiment. Referring to FIG. 8, a screen displayed on the display 141 as a result of step S182 being executed includes, on the left side, "7/26" and "12:03" as the current date and time, in the middle, "Up" indicating that the display relates to ascent, and, on the right side, the characters "Walk" indicating that the display relates to the case of walking or running, the characters "Auto" indicating that the display relates to the case where a lift device was used, "3F" as the value of the number of ascended floors, which is the value in the case of Walk, and "4F" as the value of the number of automatically ascended floors, which is the value in the case of Auto.

Returning to FIG. 4B, if it is judged that the number of ascended floors and the number of automatically ascended floors is not being displayed, and that display has not been switched to the number of ascended floors and the number of automatically ascended floors (if judged NO at step S181), the control unit 110, at step S183, judges whether the number of descended floors, which corresponds to the number of ascended floors described at step S117 of FIG. 5, and the number of automatically descended floors described at step S136 of FIG. 6 are being displayed, or whether an operation for switching display to the number of descended floors and the number of automatically descended floors has been performed as a result of the change display/enter switch 131 of the operation unit 130 being operated.

If it is judged that the number of descended floors and the number of automatically descended floors are being displayed, or that display has been switched to the number of descended floors and the number of automatically descended floors (if judged YES at step S183), the control unit 110, at step S184, respectively reads out, from the memory 120, the number of descended floors stored in the memory 120 and the number of automatically descended floors counted and stored in the memory 120 at step S136 of FIG. 6, and transmits a control signal to the display unit 140 so as to displayed the read values on the display 141.

Figure 9:
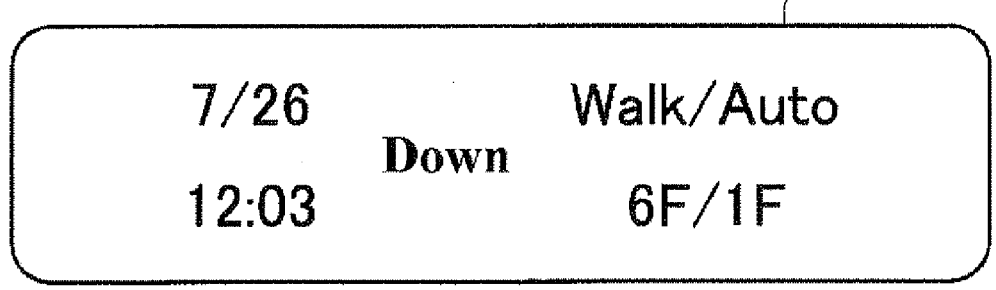
FIG. 9 shows a second exemplary display that is displayed on the activity monitor according to the first embodiment.

FIG. 9 shows a second exemplary display that is displayed on the activity monitor 100 according to the first embodiment. Referring to FIG. 9, a screen displayed on the display 141 as a result of step S184 being executed includes, on the left side, "7/26" and "12:03" as the current date and time, in the middle, "Down" indicating that the display relates to descending, and, on the right side, the characters "Walk" indicating that the display relates to the case of walking or running, the characters "Auto" indicating that the display relates to the case of using a lift device, "6F" as the value of the number of descended floors, which is the value for in the case of Walk, and "1F" as the value of the number of automatically descended floors, which is the value in the case of Auto.

Figure 4B:
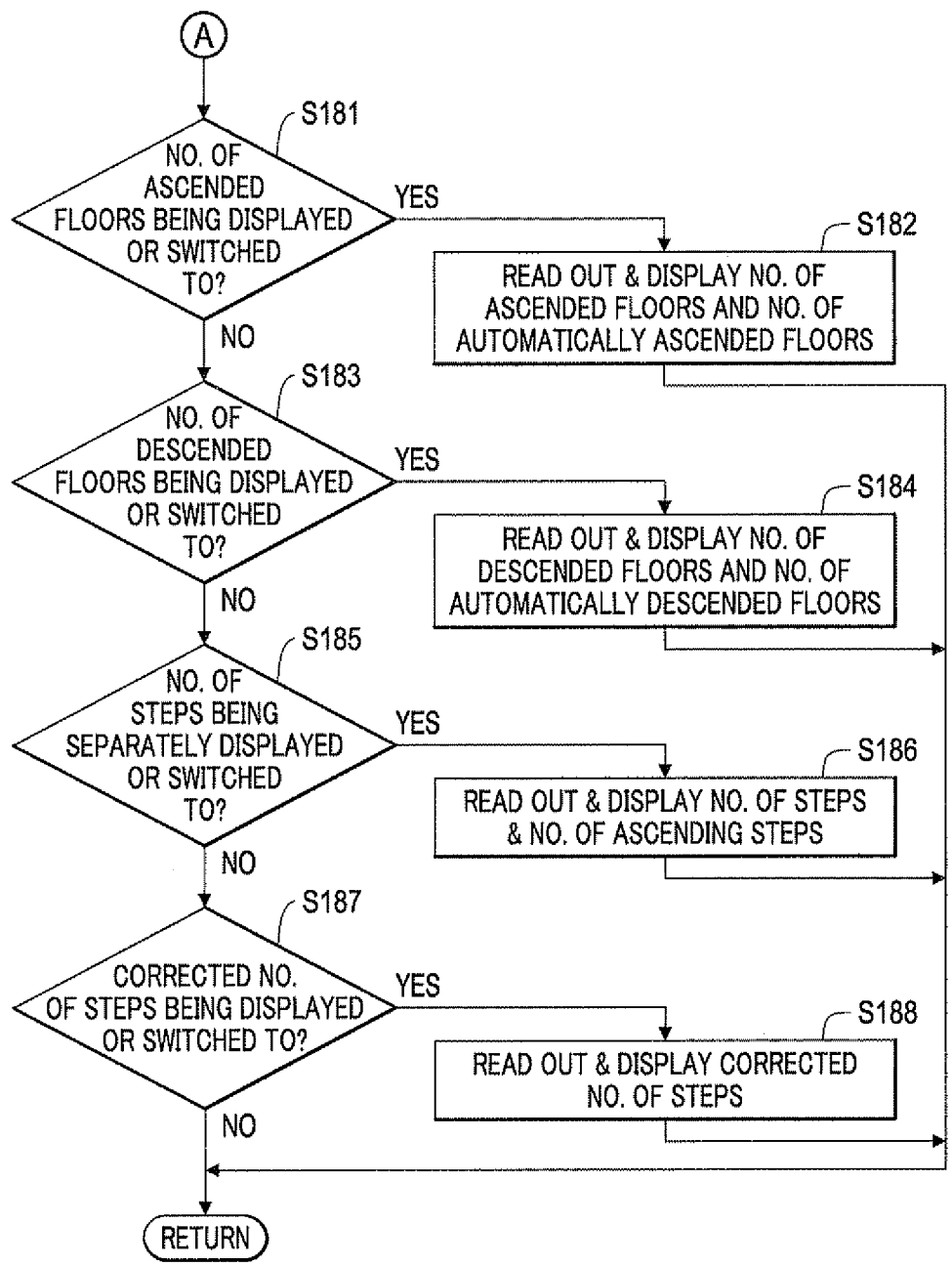

Returned to FIG. 4B, if it is judged that the number of descended floors and the number of automatically descended floors are not being displayed, and that display has not been switched to the number of descended floors and the number of automatically descended floor (if judged NO at step S183), the control unit 110, at step S185, judges whether the accumulated number of steps described at step S172 and the number of ascending steps described at step S174 are being displayed, or whether an operation for switching display to the accumulated number of steps and the number of ascending steps has been performed as a result of the change display/enter switch 131 of the operation unit 130 being operated.

If it is judged that the accumulated number of steps and the number of ascending steps are being displayed, or that display has been switched to the accumulated number of steps and the number of ascending steps (if judged YES at step S185), the control unit 110, at step S186, respectively reads out, from the memory 120, the accumulated number of steps counted and stored in the memory 120 at step S172 and the number of ascending steps counted and stored in the memory 120 at step S174, and transmits an operation signal to the display unit 140 so as to cause the read values to be displayed on the display 141.

Figure 10:
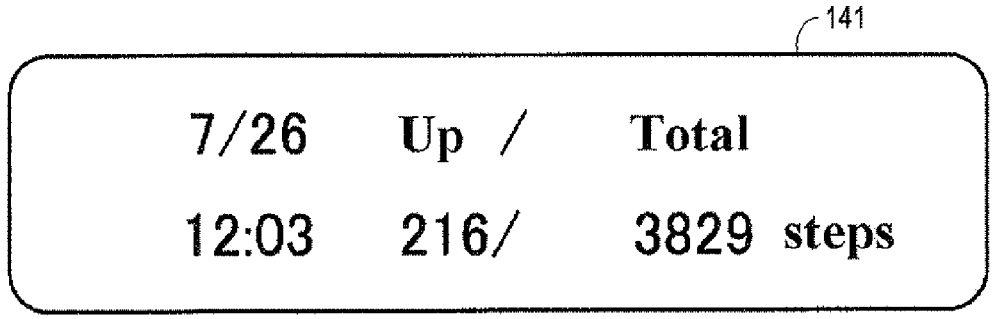
FIG. 10 shows a third exemplary display that is displayed on the activity monitor according to the first embodiment.

FIG. 10 shows a third exemplary display that is displayed on the activity monitor 100 according to the first embodiment. Referring to FIG. 10, a screen displayed on the display 141 as a result of step S186 being executed includes, on the left side, "7/26" and "12:03" as the current date and time, in the middle, the characters "Up" indicating that the display relates to the number of ascending steps and "216" steps as the value of the number of ascending steps, and, on the right side, the characters "Total" indicating that the display relates to the accumulated number of steps and "3829 steps" as the value of the accumulated number of steps.

Returning to FIG. 4B, if it is judged that the accumulated number of steps and the number of ascending steps are not being displayed, and that display has not been switched to the accumulated number of steps and the number of ascending steps (if judged NO at step S185), the control unit 110, at step S187, judges whether a corrected number of steps obtained by correcting the accumulated number of steps described at step S172 is being displayed, or whether an operation for switching display to the corrected number of steps has been performed as a result of the change display/enter switch 131 of the operation unit 130 being operated.

If it is judged that the corrected number of steps is being displayed or that display has been switched to the corrected number of steps (if judged YES at step S187), the control unit 110, at step S188, reads out, from the memory 120, an accumulated number of steps a counted and stored in the memory 120 at step S172 (includes the number of ascending steps) and a number of ascending steps b counted and stored in the memory 120 at step S174, and calculates a corrected number of steps $c=a-b+b\times(8/3)=a+b\times(5/3)$.

Here, according to "Physical Activity Indicators for Healthy Living" (Exercise Guide 2006) created by the Ministry of Health, Labour and Welfare, physical activity intensity in the case of walking normally on level ground and descending stairs is 3 METS, while physical activity intensity in the case of ascending stairs is 8 METS. According to this, as mentioned above, by adding a value obtained by multiplying the number of ascending steps b by 8/3, which is the ratio of physical activity intensity in the case of ascending stairs relative to walking normally, to a value obtained by subtracting the number of ascending steps b from the accumulated number of steps a, the accumulated number of steps a, which includes the number of ascending steps b, can be corrected to a corrected number of steps c converted to the case of walking normally.

Note that although the case of walking is considered in the present embodiment, a corrected number of steps can also be calculated in the case of running, by counting the respective numbers of steps for running on level ground, ascending by running and descending by running, similarly to the case of walking.

At step S188, the control unit 110 then transmits a control signal to the display unit 140 so as to cause the corrected number of steps that has been calculated to be displayed on the display 141.

Figure 11:
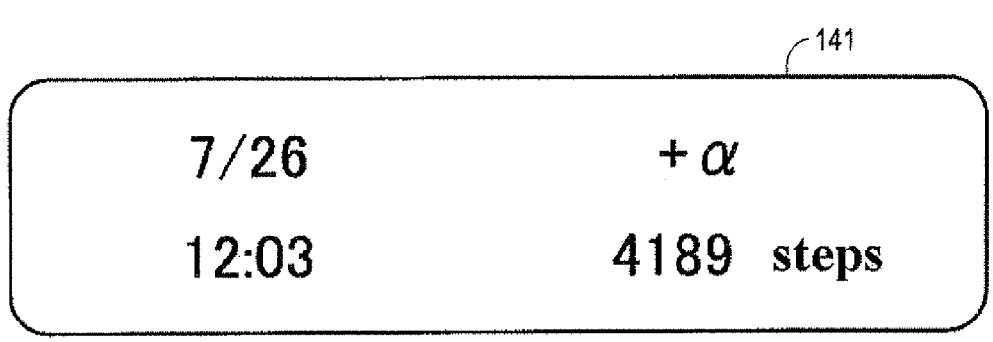
FIG. 11 shows a fourth exemplary display that is displayed on the activity monitor according to the first embodiment.

FIG. 11 shows a fourth exemplary display that is displayed on the activity monitor 100 according to the first embodiment. Referring to FIG. 11, a screen displayed on the display 141 as a result of step S188 being executed includes, on the left side, "7/26" and "12:03" as the current date and time, and, on the right side, the characters "+α" indicating that the display relates to a corrected number of steps and "4189 steps" as the value of the corrected number of steps.

Here, the corrected number of steps c can be calculated, using an abovementioned equation, from the accumulated number of steps a=3829 steps and the number of ascending steps b=216 steps shown in FIG. 10 as $c=a+b\times(5/3)=3829+216\times(5/3)=4189$ steps.

Returning to FIG. 4B, if it is judged that the corrected number of steps is not being displayed, and that display has not been switched to the corrected number of steps (if judged NO at step S187), or after step S182, step S184, step S186 or step S188, the control unit 110 returns to the processing from which this body movement detection and display processing was originally called.

Variation of First Embodiment

In the abovementioned embodiment, as illustrated in FIG. 5, it is judged whether the user has started or stopped ascending/descending based on the detection values of the acceleration sensor 170, and when it is judged that the user has stopped ascending/descending this time after having judged that the user has started ascending/descending last time, 1 is added to the number of ascended/descended floors when it is judged that roughly the number of stairs for one floor has been reached, having judged that the user has ascended/descended roughly one flight of stairs that do not have a landing between floors, whereas when it is judged that the user has stopped ascending/descending this time after having judged that the user has started ascending/descending the time before last, 1 is added to the number of ascended/descended floors when it is judged that roughly the number of stairs for one floor has been reached, having judged that the user has ascended/descended roughly one flight of stairs that do have a landing between floors.

Figure 12:
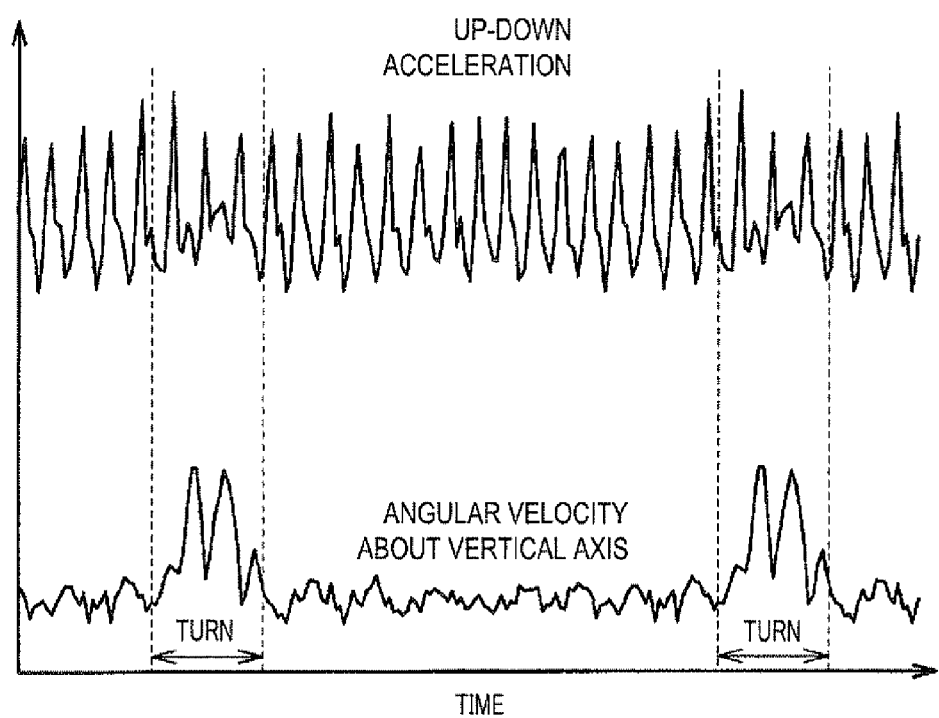
FIG. 12 is a graph for illustrating ascent/descent detection using a gyro sensor according to a variation of the first embodiment.

FIG. 12 is a graph for illustrating ascent/descent detection using a gyro sensor according to the variation of the first embodiment. Referring to FIG. 12, when a gyro sensor is used, a change is observed in angular velocity about the vertical axis when the user turns on a landing.

Thus, it is judged that the user has started or stopped ascending/descending stairs when a change is observed in the detection values of the gyro sensor, and when it is judged that the user has stopped ascending/descending this time after having judged that the user has started ascending/descending last time, 1 is added to the number of ascended/descended floors when it is judged that the number of stairs for roughly one floor has been reached, having judged that the user has ascended/descended roughly one flight of stairs that do not have a landing between floors, whereas when it is judged that the user has stopped ascending/descending this time after having judged that the user has started ascending/descending the time before last, 1 is added to the number of ascended/descended floors when it is judged that roughly the number of stairs for one floor has been reached, having judged that the user has ascended/descended roughly one flight of stairs that do have a landing between floors.

In other words, the number of floors that the user has ascended may be calculated, based on the number of times that the user turns, which is calculated based on detection values from a gyro sensor.

Second Embodiment

In the first embodiment, as illustrated in FIG. 5, the number of ascended/descended floors is calculated, based on detection values for acceleration from the acceleration sensor 170, when it is detected that the user has ascended/descended. In the second embodiment, the number of ascended/descended floors is calculated, based on detection values for atmospheric pressure from the atmospheric pressure sensor 180, when it is detected that the user has ascended/descended.

Also, in the first embodiment, as illustrated in FIG. 4B, the number of ascended/descended floors in the case where the user does not use a lift device and in the case where the user does use a lift device are displayed. In the second embodiment, the number of times that the user does not use a lift device and the number of times that the user does use a lift device per ascent/descent or per number of ascended/descended floors is displayed.

Figure 13A:
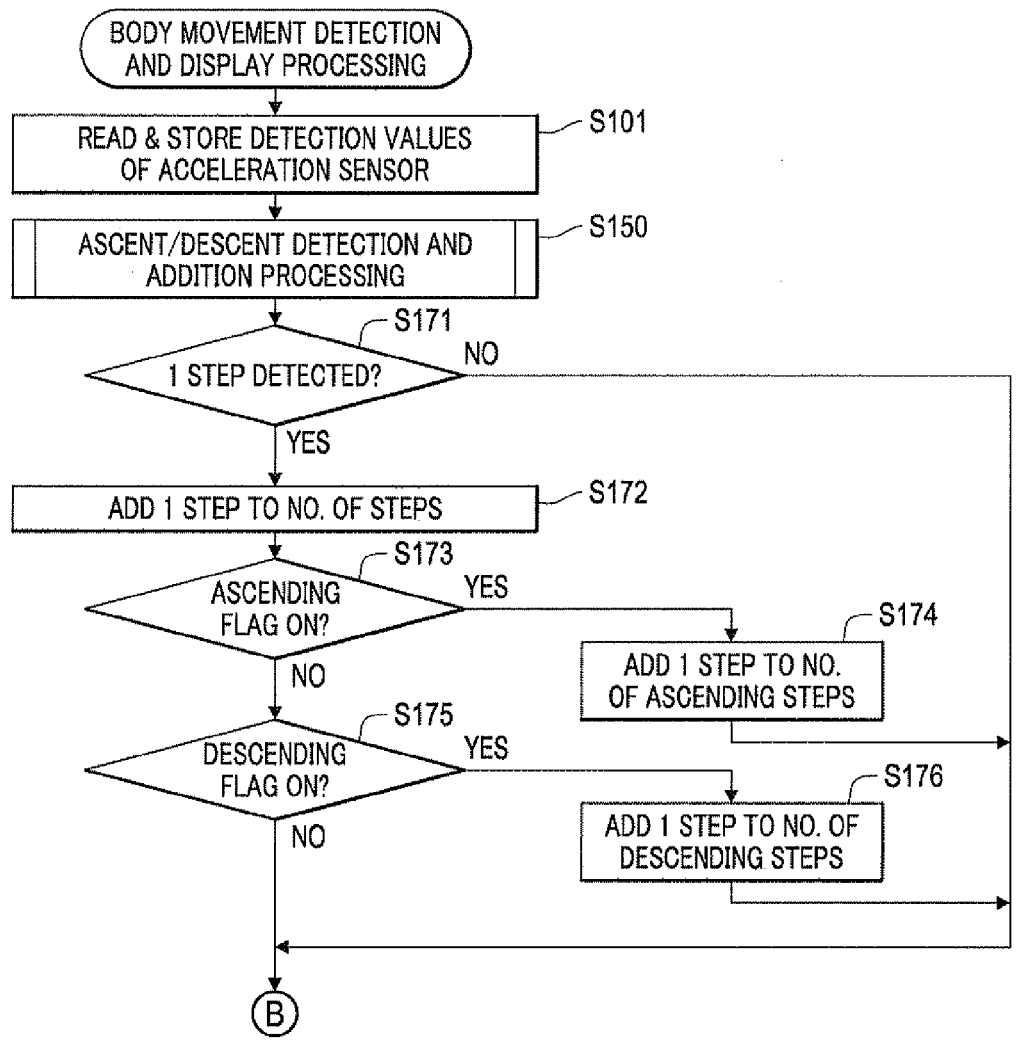
FIGS. 13A and 13B are flowcharts showing the flow of body movement detection and display processing executed by the activity monitor according to a second embodiment.

FIG. 13A is a flowchart showing the flow of body movement detection and display processing executed by the activity monitor according to the second embodiment. Referring to FIG. 13A, because the processing of step S101 and the processing from steps S171 to S176 and from steps S185 to S188 is similar to the body movement detection and display processing of FIG. 4B, redundant description will not be repeated.

Figure 14A:
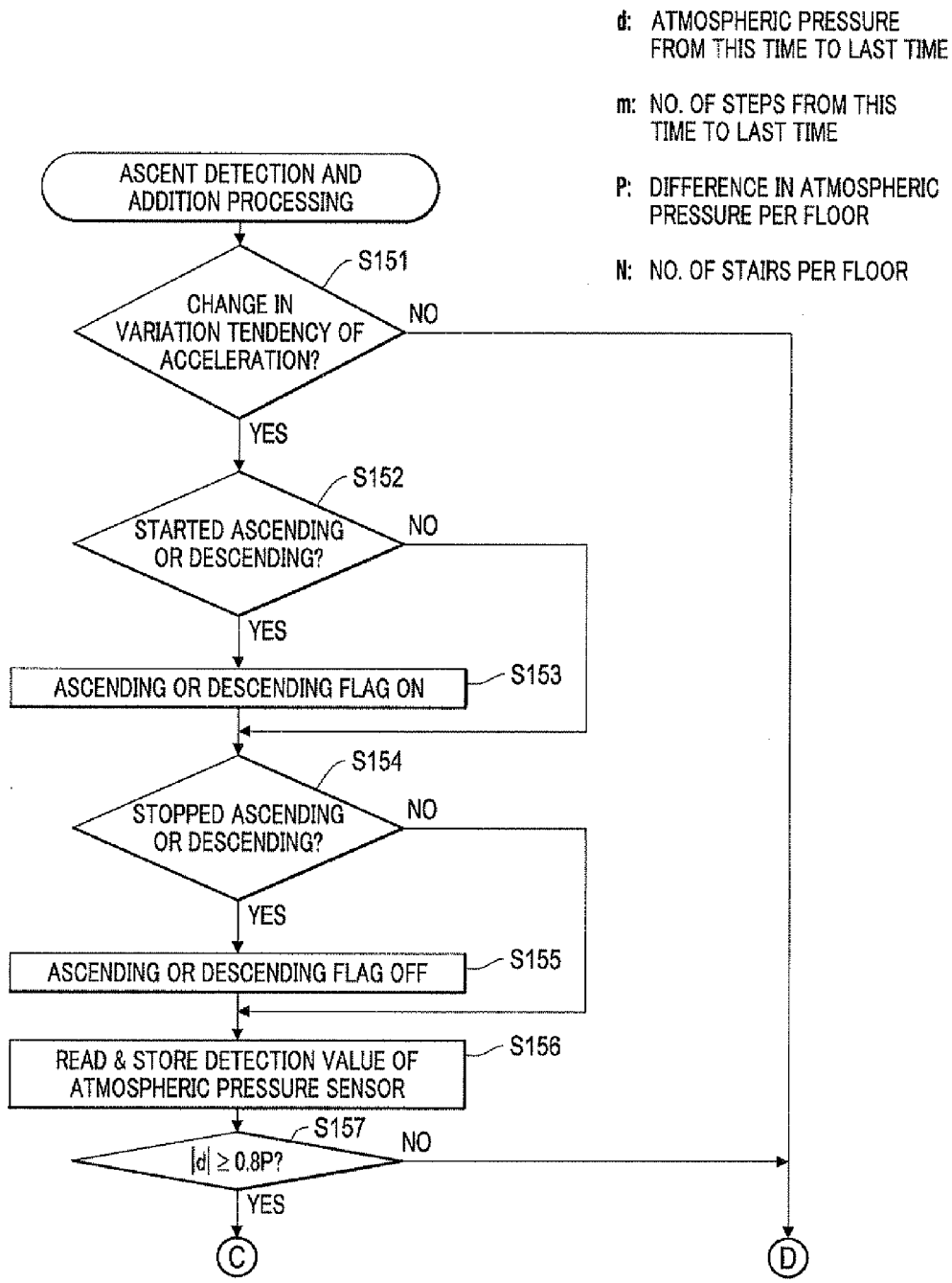
FIGS. 14A and 14B are flowcharts showing the flow of ascent/descent detection and addition processing executed by the activity monitor according to the second embodiment.
Figure 14B:
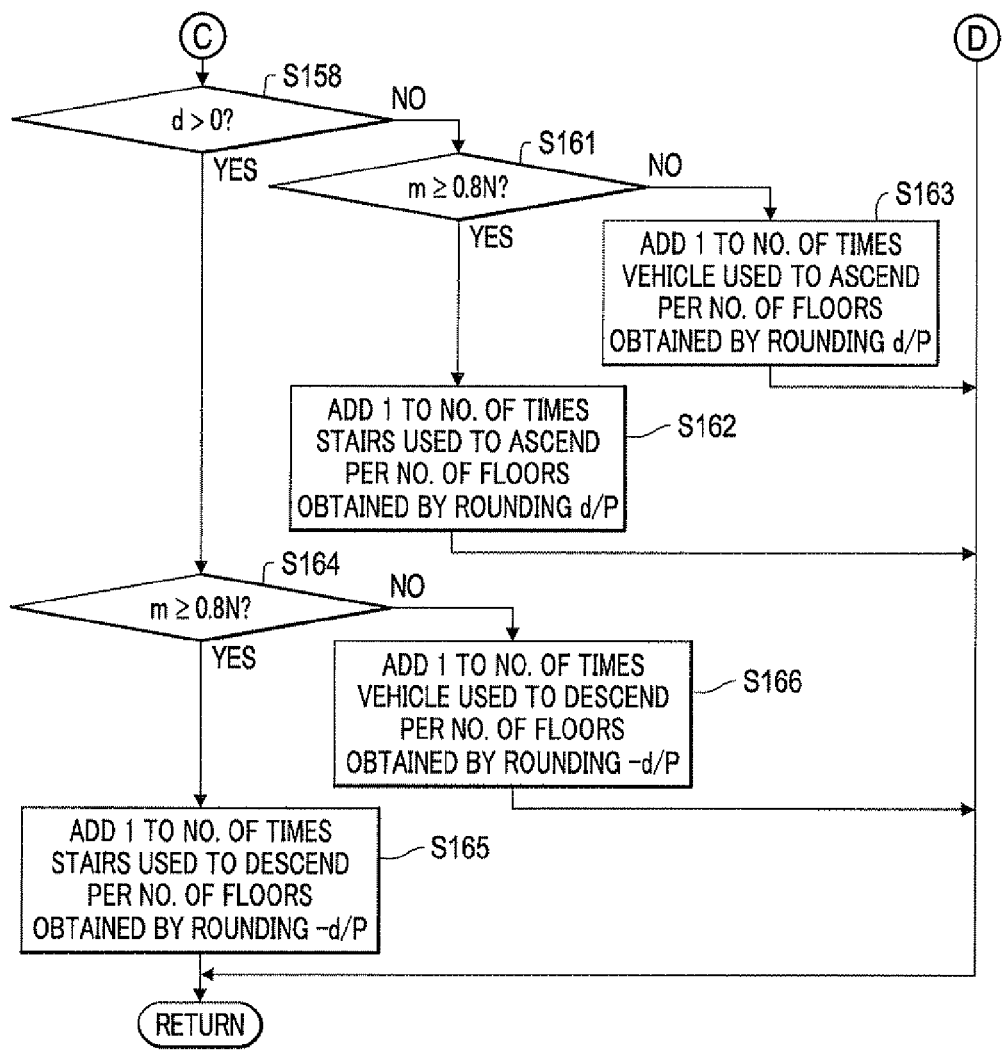

After step S101, the control unit 110, at step S150, performs ascent/descent detection and addition processing. FIGS. 14A and 14B are flowcharts showing the flow of the ascent/descent detection and addition processing executed by the activity monitor according to the second embodiment.

Referring to FIG. 14A, at step S151, the control unit 110 judges whether there has been a change in the variation tendency of detection values indicated by detection signals from the acceleration sensor 170. This processing is similar to the processing of step S131 in FIG. 6.

If it is judged that there has been a change in the variation tendency of detection values for acceleration (if judged YES at step S151), the control unit 110, at step S152, judges whether the user has started ascending or descending stairs, an incline or the like by walking. This processing is similar to the processing of step S111 in FIG. 5.

If it is judged that the user has started ascending or descending by walking (if judged YES at step S152), the control unit 110, at step S153, respectively sets the ascending flag or the descending flag to ON. This processing is similar to the processing of step S112 in FIG. 5.

If it is judged that user has not started ascending or descending by walking (if judged NO at step S152), or after step S153, the control unit 110, at step S154, judges whether the user has stopped ascending or descending by walking. This processing is similar to the processing of step S113 in FIG. 5.

If it is judged that the user has stopped ascending or descending by walking (if judged YES at step S154), the control unit 110, at step S155, respectively sets the ascending flag or the descending flag to OFF. This processing is similar to the processing of step S114 in FIG. 5.

If it is judged that the user has not stopped ascending or descending by walking (if judged NO at step S154), or after step S155, the control unit 110, at step S156, reads the detection value indicated by the detection signal from the atmospheric pressure sensor 180, and stores the read detection value in the memory 120. This processing is similar to the processing of step S132 in FIG. 6.

Next, at step S157, the control unit 110 judges whether the difference in atmospheric pressure d obtained by subtracting the detection value for atmospheric pressure when it was judged that there was a change in the variation tendency of acceleration last time from the detection value for atmospheric pressure when it was judged that there was change in the variation tendency of acceleration this time, or in other words, the absolute value of the difference in atmospheric pressure d after there was a change in the variation tendency of acceleration last time until there was a change in the variation tendency of acceleration this time, is greater than or equal to 0.8 times the difference in atmospheric pressure P equivalent to one floor. This processing is similar to the processing of step S134 in FIG. 6.

If it is judged that the absolute value |d| of the difference in atmospheric pressure between last time and this time is greater than or equal to 0.8 times the difference in atmospheric pressure P for one floor (if judged YES at step S157), the control unit 110, at step S158, judges whether the difference in atmospheric pressure d between last time and this time is greater than zero, or in other words, whether the difference in atmospheric pressure d is positive. This processing is similar to step S135 in FIG. 6.

If it is judged that the difference in atmospheric pressure d is not positive (if judged NO at step S158), the control unit 110, at step S161, judges whether the number of steps m obtained by subtracting the accumulated number of steps when it was judged that there was a change in the variation tendency of acceleration last time from the accumulated number of steps when it was judged that there was a change in the variation tendency of acceleration this time, or in other words, the number of steps m after there was a change in the variation tendency of acceleration last time until there was a change in the variation tendency of acceleration this time, is greater than or equal to 0.8 times the number of stairs N equivalent to one floor.

Because it is conceivable that the user ascended by walking in the case where it is judged that the number of steps m from last time until this time is greater than or equal to 0.8 times the number of stairs N for one floor (if judged YES at step S161), the control unit 110, at step S162, adds 1 to the number of times stairs were used to ascend per number of floors obtained by dividing the difference in atmospheric pressure d between last time and this time by the difference in atmospheric pressure P for one floor and rounding the resultant value. The number of times stairs were used to ascend per number of floors denotes the number of times that the user used stairs per number of ascended floors in one ascent of stairs. The number of times stairs were used to ascend per number of floors is stored in the memory 120.

On the other hand, because it is conceivable that the user ascended using a lift device in the case where it is judged that the number of steps m from last time until this time is not greater than or equal to 0.8 times the number of stairs N for one floor (if judged NO at step S161), the control unit 110, at step S163, adds 1 to the number of times that a vehicle was used to ascend per number of floors obtained by dividing the difference in atmospheric pressure d between last time and this time by the difference in atmospheric pressure P for one floor and rounding the resultant value. The number of times that a vehicle was used to ascend per number of floors denotes the number of times that the user used a lift device per number of ascended floors in one ascent using a lift device. The number of times that a vehicle was used to ascend per number of floors is stored in the memory 120.

If it is judged that the difference in atmospheric pressure d is positive (if judged YES at step S158), the control unit 110, at step S164, judges whether the number of steps m obtained by subtracting the accumulated number of steps when it was judged that there was a change in the variation tendency of acceleration last time from the accumulated number of steps when it was judged that there was a change in the variation tendency of acceleration this time, or in other words, the number of steps m after there was a change in the variation tendency of acceleration last time until there was a change in the variation tendency of acceleration this time, is greater than or equal to 0.8 times the number of stairs N equivalent to one floor.

Because it is conceivable that the user descended by walking in the case where it is judged that the number of steps m from last time until this time is greater than or equal to 0.8 times the number of stairs N for one floor (if judged YES at step S164), the control unit 110, at step S165, adds 1 to the number of times stairs were used to descend per number of floors obtained by dividing the difference in atmospheric pressure d between last time and this time by the difference in atmospheric pressure P for one floor, reversing the plus/minus sign and rounding the resultant value. The number of times stairs were used to descend per number of floors denotes the number of times the user used stairs to descend per number of floors in one descent of stairs. The number of times stairs were used to descend per number of floors is stored in the memory 120.

On the other hand, because it is conceivable that the user descended using a lift device in the case where it is judged that the number of steps m from last time until this time is not greater than or equal to 0.8 times the number of stairs N for one floor (if judged NO at step S164), the control unit 110, at step S166, adds 1 to the number of times a vehicle was used to descend per number of floors obtained by dividing the difference in atmospheric pressure d between last time and this time by the difference in atmospheric pressure P for one floor, reversing the plus/minus sign and rounding the resultant value. The number of times a vehicle was used to descend per number of floors denotes the number of times the user used a lift device to descend per number of floors in one descent using a lift device. The number of times a vehicle was used to descend per number of floors is stored in the memory 120.

If it is judged that there is no change in the variation tendency of acceleration (if judged NO at step S151), if it is judged that the absolute value |d| of the difference in atmospheric pressure between last time and this time is not greater than or equal to 0.8 times the difference in atmospheric pressure P for one floor (if judged NO at step S157), or after step S162, step S163, step S165 or step S166, the control unit 110 returns to the body movement detection and display processing from which this ascent/descent detection and addition processing was originally called.

In this way, it is clear when the user is deemed to have started or stopped ascending/descending as a result of changes in the variation tendency of acceleration, and when it is judged that the difference in atmospheric pressure d between when the user is deemed to have started ascending/descending and when the user is deemed to have stopped ascending/descending has reached roughly the difference in atmospheric pressure P for one floor, 1 is added to the number of times stairs were used to ascend or the number of times stairs were used to descend per number of floors, according to the number of floors that the user ascended/descended, in the case where it is deemed that the change of the number of steps during that period has reached the number of stairs N for one floor, whereas 1 is added to the number of times a vehicle was used to ascend or the number of times that a vehicle was used to descend per number of floors, according to the number of floors that the user ascended/descended, in the case where it is deemed that the change of the number of steps during that period has not reached the number of stairs N for one floor.

Here, because the judgment at steps S161 and S164 involves judging whether the method by which the user ascended/descended was walking or a lift device, the scaling value may be smaller than 0.8 times the number of stairs N for one floor. Because the user may, however, walk several steps while riding a lift device, the scaling factor desirably is greater than or equal to the number of steps that the user walks while riding a lift device.

Figure 13B:
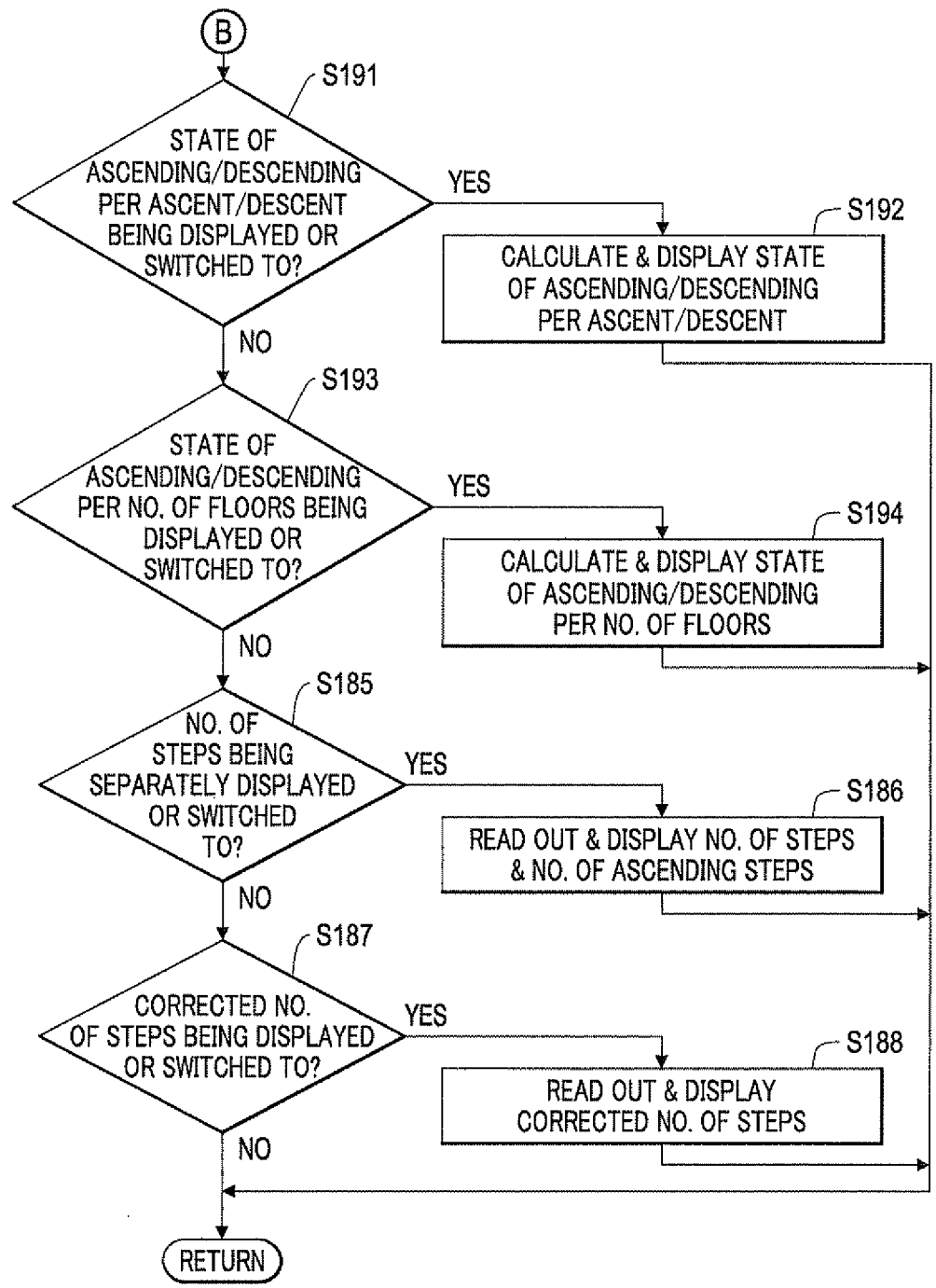

Returning to FIG. 13B, in the case where the processing proceeds to step S191, the control unit 110 judges whether the state of ascending/descending per ascent/descent is being displayed, or whether an operation for switching display to the state of ascending/descending per ascent/descent has been performed as a result of the change display/enter switch 131 of the operation unit 130 being operated.

If it is judged that the state of ascending/descending per ascent/descent is being displayed, or that display has been switched to the state of ascending/descending per ascent/descent (if judged YES at step S191), the control unit 110, at step S192, calculates the number of times stairs were used and the number of times a vehicle was used per ascent and descent, from the number of times stairs were used to ascend per number of floors, the number of times a vehicle was used to ascend per number of floors, the number of times stairs were used to descend per number of floors, and the number of times a vehicle was used to descend per number of floors that are counted and stored in stored in the memory 120 at steps S162, S163, S165 and S166 in FIG. 14B, and transmits a control signal to the display unit 140 so as to cause the calculated values to be displayed on the display 141.

Figure 15:
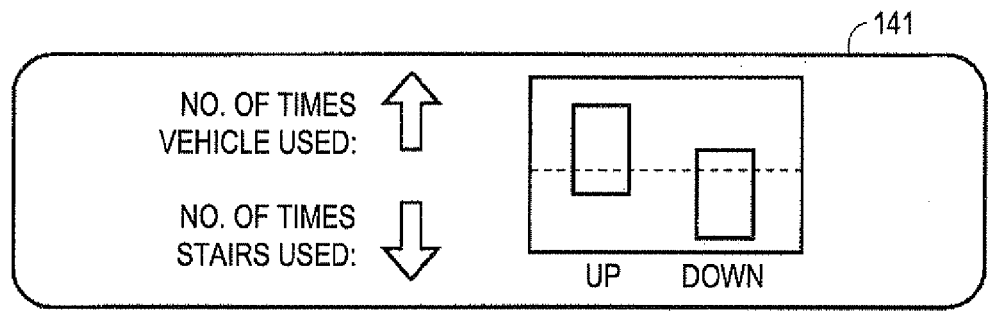
FIG. 15 shows a first exemplary display that is displayed on the activity monitor according to the second embodiment.

FIG. 15 shows a first exemplary display that is displayed on the activity monitor 100 according to the second embodiment. Referring to FIG. 15, a screen displayed on the display 141 as a result of step S192 being executed includes, on the left side, the characters "No. of times vehicle used" indicating that the upper half of the right-hand graph relates to the number of times that a vehicle was used, and the characters "No. of times stairs used" indicating that the lower half of the right-hand graph relates to the number of times that stairs were used, and, on the right side, a graph indicating the number of times stairs were used and the number of times a vehicle was used per ascent and descent.

Returning to FIG. 13B, if it is judged that the state of ascending/descending per ascent/descent is not being displayed, and that display has not been switched to the state of ascending/descending per ascent/descent (if judged NO at step S191), the control unit 110, at step S193, judges whether the state of ascending/descending per number of floors is being displayed, or whether an operation for switching display to the state of ascending/descending per number of floors has been performed as a result of the change display/enter switch 131 of the operation unit 130 being operated.

If it is judged that the state of ascending/descending per number of floors is being displayed, or that display has been switched to the state of ascending/descending per number of floors (if judged YES at step S193), the control unit 110, at step S194, calculates the number of times stairs were used and the number of times a vehicle was used per number of floors, from the number of times stairs were used to ascend per number of floors, the number of times a vehicle was used to ascend per number of floors, the number of times stairs were used to descend per number of floors, and the number of times a vehicle was used to descend per number of floors that were counted and stored in the memory 120 at steps S162, S163, S165 and S166 in FIG. 14B, and transmits a control signal to the display unit 140 so as to cause the calculated values to be displayed on the display 141.

Figure 16:
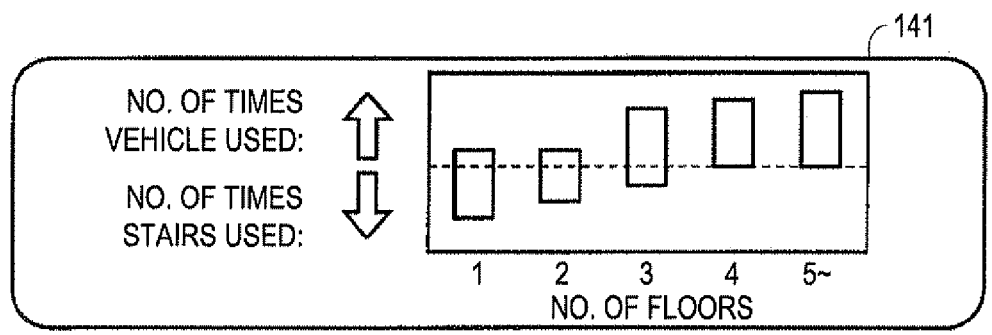
FIG. 16 shows a second exemplary display that is displayed on the activity monitor according to the second embodiment.

FIG. 16 shows a second exemplary display that is displayed on the activity monitor 100 according to the second embodiment. Referring to FIG. 16, a screen displayed on the display 141 as a result of step S192 being executed includes, on the left side, the characters "No. of times vehicle used" indicating that the upper half of the right-hand graph relates to the number of times that a vehicle was used, and the characters "No. of times stairs used" indicating that the lower half of the right-hand graph relates to the number of times that stairs were used, and, on the right side, a graph showing the number of times stairs were used and the number of times a vehicle was used per number of ascended and descended floors in one movement.

Next, variations of the abovementioned embodiments will be described.

(1) In the aforementioned first and second embodiments, it is judged that the user has started or stopped ascending/descending stairs, when there is a change in the variation tendency of detection values for acceleration from the acceleration sensor 170. However, the present invention is not limited thereto, and it may be judged that the user has started or stopped ascending/descending stairs, when there is a change in the detection values for atmospheric pressure from the atmospheric pressure sensor 180.

In other words, although it was detected whether the user is ascending/descending based on detection values from the acceleration sensor 170 in the aforementioned embodiments, it may be detected whether the user is ascending/descending based on detection values from the atmospheric pressure sensor 180.

(2) In the abovementioned first embodiment, the number of ascended floors, the number of descended floors, the number of automatically ascended floors and the number of automatically descended floors are counted and displayed, as illustrated from FIGS. 4A to 6 and in FIGS. 8 and 9.

However, the present invention is not limited thereto, and instead of counting the number of ascended floors, the number of descended floors, the number of automatically ascended floors and the number of automatically descended floors, the number of times that the user did not use a lift device and the number of times that the user did use a lift device per ascent/descent or per number of ascended/descended floors may be counted and displayed.

(3) In the aforementioned second embodiment, the number of times that the user did not use a lift device and the number of times that the user did use a lift device per ascent/descent or per number of ascended/descended floors is counted and displayed, as illustrated from FIGS. 13A to 16.

However, the present invention is not limited thereto, and instead of counting the number of times that the user did not use the lift device and the number of times that the user did use the lift device per ascent/descent or per number of ascended/descended floors, the number of ascended floors, the number of descended floors, the number of automatically ascended floors, and the number of automatically descended floors may be counted and displayed.

(4) In the aforementioned embodiments, as illustrated in FIGS. 14A and 14B, in the case where the difference between the detection value for atmospheric pressure when there was a change in the variation tendency of acceleration this time and the detection value for atmospheric pressure when there was a change in the variation tendency of acceleration last time has reached roughly the difference in atmospheric pressure P for one floor, it is assumed that the user ascended/descended by walking in the case where the change in the number of steps during that period is deemed to have reached roughly the number of stairs N for one floor, and it is assumed that the user ascended/descended by a lift device in the case where the change in the number of steps during that period is deemed to have not reached roughly the number stairs N for one floor.

However, the present invention is not limited thereto, and it may be judged that the user is ascending/descending by walking in the case where there is a change in the variation tendency of acceleration and there is change in atmospheric pressure, and it may be judged that the user is ascending/descending by a lift device in the case where there is no change in the variation tendency of acceleration and there is change in atmospheric pressure.

Furthermore, it may be judged that the user ascended/descended by a lift device in the case where a change in atmospheric pressure is no longer detected and a change in the variation tendency of acceleration is detected, after detecting no change in the variation tendency of acceleration and a change in the variation tendency of atmospheric pressure, and it may be judged that the user ascended/descended by car, train or the like in the case where no change in the variation tendency of acceleration is detected even though a change in atmospheric pressure is no longer detected.

(5) The embodiments disclosed herein are to be considered in all respects as illustrative and not restrictive. The technical scope of the invention is defined by the claims, and all changes that come within the meaning and range of equivalency of the claims are intended to be embraced therein.

REFERENCE SIGNS LIST

100 Activity monitor
110 Control unit
120 Memory
130 Operation unit
131 Change display/enter switch
132 Left operation/memory switch
133 Right operation switch
140 Display unit
141 Display
170 Acceleration sensor
180 Atmospheric pressure sensor
190 Power source
191 Main body
192 Clip

The invention claimed is:

1. A body movement detection device comprising a main body, a display unit and a control unit, the control unit including:
   a movement detector that detects that a user who is wearing or carrying the main body is ascending or descending floors using a lift device, or using stairs;
   an electronic counter for counting:
      separately for different number of floors changed in one movement: (1) a number of times the user used the lift device to ascend or descend floors, and (2) a number of times the user used the stairs to ascend or descend floors, based on a detection result of the movement detector; and
   a display module, operable on a processor, that instructs the display unit to display, separately for different number of floors: (1) a number of times the user used the lift device to ascend or descend floors, and (2) a number of times the user used the stairs to ascend or descend floors.

2. The body movement detection device according to claim 1, wherein the counter counts the number of times that the user ascends or descends using the lift device and the number of times that the user ascends or descends without using the lift device, per ascent and descent by (1) setting an ascending flag when the user is ascending and counting the number of ascending steps only while the ascending flag is set and (2) setting a descending flag when the user is descending and counting the number of descending steps only while the descending flag is set.

3. The body movement detection device according to claim 1, wherein the counter counts the number of times that the user ascends or descends using the lift device and the number of times that the user ascends or descends without using the lift device, per number of floors that the user has ascended or descended.

4. The body movement detection device according to claim 1 further comprising:
   an acceleration sensor for detecting acceleration of the main body; and
   an atmospheric pressure sensor for detecting an ambient atmospheric pressure of the main body,
   wherein the movement detector detects whether the user is ascending or descending using the lift device, based on a detection result from the acceleration sensor and a detection result from the atmospheric pressure sensor.

* * * * *